(12) United States Patent
Masson et al.

(10) Patent No.: US 12,718,915 B2
(45) Date of Patent: Aug. 25, 2026

(54) SYSTEM AND METHOD FOR CONTINUOUSLY OPTIMIZING MEDICAL REFERENCE MANUALS

(71) Applicant: EXPANDED EXISTENCE, INC., Windermere, FL (US)

(72) Inventors: Robert L. Masson, Windermere, FL (US); Raymond G. Oktavec, Fort Lauderdale, FL (US); Kyle A. Masson, Windermere, FL (US); Brett Luc Masson, Windermere, FL (US)

(73) Assignee: EXPANDED EXISTENCE, INC., Windermere, FL (US)

( * ) Notice: Subject to any disclaimer, the term of this patent is extended or adjusted under 35 U.S.C. 154(b) by 219 days.

(21) Appl. No.: 18/470,562

(22) Filed: Sep. 20, 2023

(65) Prior Publication Data

US 2025/0095812 A1 Mar. 20, 2025

(51) Int. Cl.
*G16H 15/00* (2018.01)
*G06T 7/00* (2017.01)
*G16H 70/20* (2018.01)

(52) U.S. Cl.
CPC ........... *G16H 15/00* (2018.01); *G06T 7/0012* (2013.01); *G16H 70/20* (2018.01); *G06T 2207/10016* (2013.01); *G06T 2207/20081* (2013.01)

(58) Field of Classification Search
CPC ........ G16H 15/00; G16H 70/20; G16H 40/20; G16H 40/00
See application file for complete search history.

(56) References Cited

U.S. PATENT DOCUMENTS

2007/0293998 A1 12/2007 Underdal
2020/0273575 A1* 8/2020 Wolf .................... A61B 5/1032
(Continued)

FOREIGN PATENT DOCUMENTS

WO WO-2024145110 A1 * 7/2024 ............. G16H 15/00

OTHER PUBLICATIONS

Hashimoto, Daniel A., et al. "Computer vision analysis of intraoperative video: automated recognition of operative steps in laparoscopic sleeve gastrectomy." Annals of surgery 270.3 (2019): 414-421. (Year: 2019).*
(Continued)

*Primary Examiner* — Constantine Siozopoulos
(74) *Attorney, Agent, or Firm* — Sagacity Legal, PLLC

(57) ABSTRACT

A system for continuously optimizing a medical reference manual for a type of medical procedure is described. The system includes one or more imaging devices and a server. Each imaging device is configured to capture a plurality of video frames associated with execution of the medical procedure. The server is configured to process the video frames to identify a medical item and a medical practitioner, identify one or more steps performed during the medical procedure, and create an operative report for the medical procedure based on the one or more steps. The server is configured to obtain one or more additional operative reports, analyze the one or more steps included in the operative report and steps included in the one or more additional operative reports to determine optimal steps for the medical procedure, and generate the medical reference manual based on the determined optimal steps.

14 Claims, 7 Drawing Sheets

(56) References Cited

U.S. PATENT DOCUMENTS

| | | | |
|---|---|---|---|
| 2020/0367974 | A1 | 11/2020 | Khalid et al. |
| 2021/0192972 | A1 | 6/2021 | Acharya et al. |

OTHER PUBLICATIONS

International Search Report and Written Opinion of the International Searching Authority dated Oct. 29, 2024 issued in International Application No. PCT/US2024/042094, filed Aug. 13, 2024.

* cited by examiner

SYSTEM AND METHOD FOR CONTINUOUSLY OPTIMIZING MEDICAL REFERENCE MANUALS

BACKGROUND OF THE INVENTION

A medical reference manual generally provides reference material and directions to doctors, medical practitioners, surgical residents, medical students, trainees, medical companies, medical device companies, and/or the like, for performing one or more medical procedures. Current methods for preparing such manuals or documentation include dictation, writing (for example, on a paper), typing (for example, on a device), and the like activities, but which are mostly manually executed and thus are time-consuming, labor intensive, fixed, and prone to error (for example, human error).

BRIEF DESCRIPTION OF THE SEVERAL VIEWS OF THE DRAWINGS

The accompanying figures, where like reference numerals refer to identical or functionally similar elements throughout the separate views, together with the detailed description below, are incorporated in and form part of the specification, and serve to further illustrate embodiments of concepts that include the claimed invention and explain various principles and advantages of those embodiments.

Figure 1:
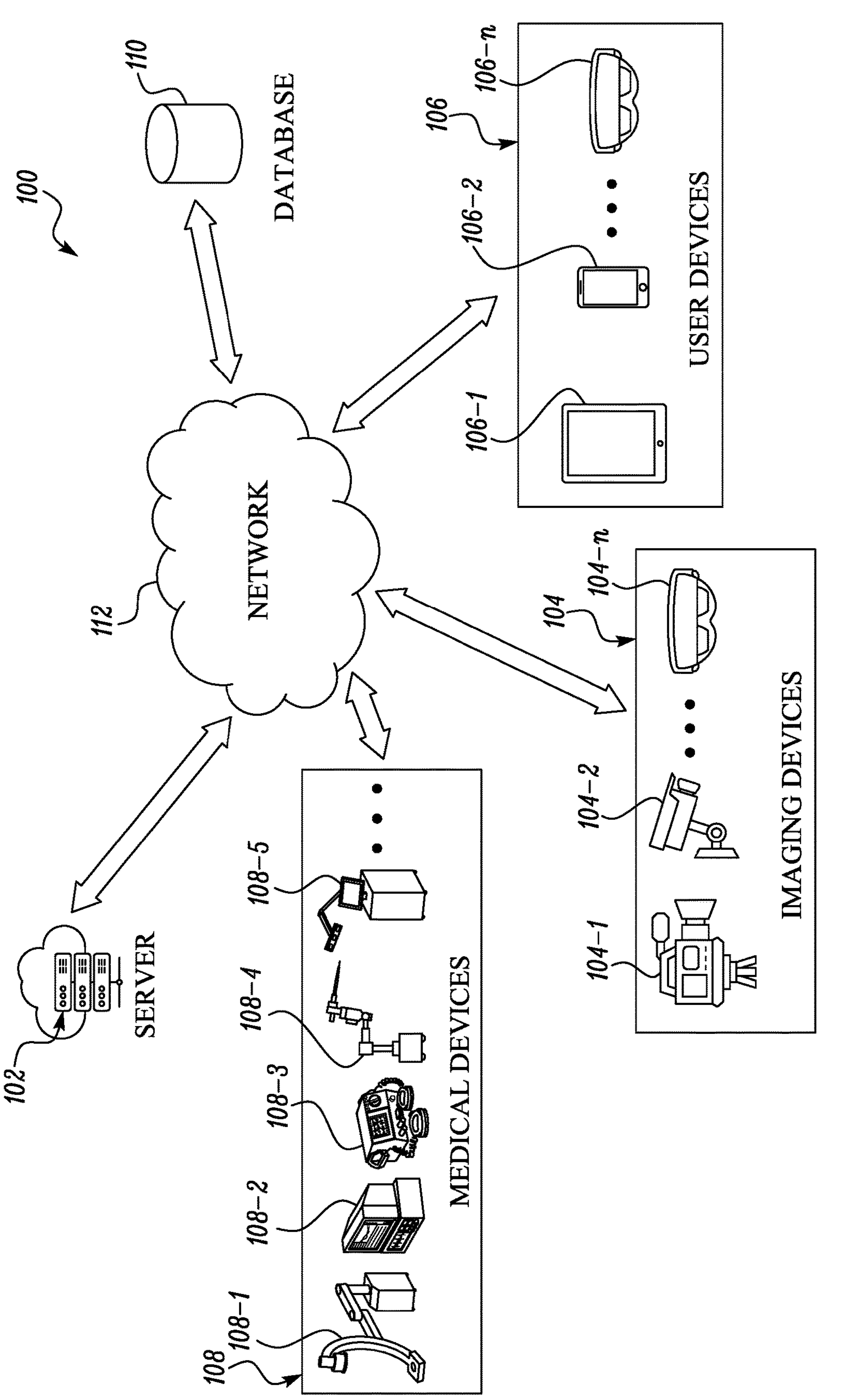
FIG. 1 is a block diagram of a system for continuously optimizing a medical reference manual for a type of medical procedure, in accordance with some embodiments.

Skilled artisans will appreciate that the elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION OF THE INVENTION

In one aspect, a system for continuously optimizing a medical reference manual for a type of a medical procedure is described. The system includes one or more imaging devices and a server communicatively coupled to the one or more imaging devices. Each imaging device is configured to capture a plurality of video frames associated with an execution of the medical procedure. The server is configured to process the plurality of video frames to identify a medical item and a medical practitioner in the plurality of video frames and analyze the plurality of video frames to determine one or more first parameters associated with the medical item and one or more second parameters associated with the medical practitioner captured in the plurality of video frames. The server is further configured to associate the one or more first parameters of the medical item with the one or more second parameters of the medical practitioner to identify one or more steps performed during the medical procedure and create an operative report for the medical procedure based on the one or more steps performed during the medical procedure. The server is further configured to obtain one or more additional operative reports associated with one or more medical procedures identical to the type of the medical procedure, analyze the one or more steps included in the operative report and steps included in the one or more additional operative reports to determine optimal steps for the medical procedure using a machine learning model, and generate the medical reference manual based on the determined optimal steps for the medical procedure.

In another aspect, a method for continuously optimizing a medical reference manual for a type of a medical procedure is described. The method includes capturing, by one or more imaging devices, a plurality of video frames associated with an execution of the medical procedure and processing, by a server, the plurality of video frames to identify a medical item and a medical practitioner in the plurality of video frames. The method further includes analyzing, by the server, the plurality of video frames to determine one or more first parameters associated with the medical item and one or more second parameters associated with the medical practitioner captured in the plurality of video frames and associating, by the server, the one or more first parameters of the medical item with the one or more second parameters of the medical practitioner to identify one or more steps performed during the medical procedure. Further, the method includes creating, by the server, an operative report for the medical procedure based on the one or more steps performed during the medical procedure and obtaining, by the server, one or more additional operative reports associated with one or more medical procedures identical to the type of the medical procedure. The method further includes analyzing, by the server, the one or more steps included in the operative report and steps included in the one or more additional operative reports to determine optimal steps for the medical procedure using a machine learning model and generating, by the server, the medical reference manual based on the determined optimal steps for the medical procedure.

FIG. 1 is a block diagram of a system 100 for continuously optimizing a medical reference manual for one or more types of medical procedures in accordance with various embodiments. The medical reference manual (also known as a presence card, a presence guide, a surgical guide, or a surgical technique guide) provides reference material and directions to one or more medical practitioners including doctors, surgical residents, medical students, trainees, and/or any other type of medical procedure staff now known or in the future developed, for performing the one or more types of medical procedures in one or more medical procedure rooms. The medical reference manual also provides the reference material to medical companies, such as, medical device manufacturing companies, to obtain data associated with execution of the one or more types of medical procedures. Each medical procedure corresponds to a plurality of steps that are to be carried out by one or more medical practitioners in a medical procedure room to improve health, treat a disease or injury or medical conditions, or make a diagnosis. For example, the type of medical procedures includes but is not limited to, spinal surgery, heart surgery, orthopedics, biopsy, or any type of procedure to diagnose, treat, or manage a medical condition, now known or in the future developed.

In accordance with various embodiments, the medical reference manual is generated based on a plurality of operative reports. Each operative report associated with a medical procedure documents the plurality of steps that are carried out by the one or more medical practitioners, a robotic system, or a combination thereto during the medical procedure in a medical procedure room. For each type of medical procedure, the system 100 generates and continuously optimizes the medical reference manual based on one or more operative reports associated with the corresponding/similar type of medical procedure performed by the same or different medical practitioner(s) in the same or different medical procedure room. For example, for spinal surgery, the system 100 generates and continuously optimizes the medical reference manual based on one or more operative reports associated with spinal surgeries performed by the same or different medical practitioner(s) in the same or different medical procedure room.

Additionally, in some embodiments, the system 100 also generates and continuously optimizes one or more medical reference manuals specific to each of the one or more medical practitioners performing the medical procedure and/or medical procedure room in which the medical procedure is performed based on requirements of the user. To this end, the system 100 is configured to obtain one or more operative reports associated with similar types of medical procedures performed by the one or more medical practitioners and/or in a medical procedure room and generate the one or more medical reference manuals specific to each medical practitioner and/or the medical procedure room. For example, for a medical practitioner 'A' performing a spinal surgery, the system 100 generates and continuously optimizes a medical reference manual for the medical practitioner 'A' based on one or more operative reports associated with the spinal surgeries performed by the medical practitioner 'A'. Additionally, or alternatively, for a medical procedure room 'X' in which a spinal surgery is performed, the system 100 generates and continuously optimizes the medical reference manual for the spinal surgeries performed in the medical procedure room 'X' based on one or more operative reports associated with the spinal surgeries performed in the medical procedure room 'X'. Additionally, or alternatively, for a medical practitioner 'A' performing a spinal surgery in the medical procedure room 'X', the system 100 generates and continuously optimizes a medical reference manual for the medical practitioner 'A' and the medical procedure room 'X' based on one or more operative reports associated with the spinal surgeries performed by the medical practitioner 'A' in the medical procedure room 'X'. Although not described herein, a person skilled in the art would appreciate that similar medical reference manuals can be generated for each medical practitioner of the one or more medical practitioners performing the medical procedure.

Referring to FIG. 1, the system 100 includes a server 102, one or more imaging devices 104 (for example, but not limited to, imaging devices 104-1, 104-2, . . . **104-*n*), one or more user devices 106 (for example, but not limited to, user devices 106-1, 106-2, . . . 106-*n*), one or more medical devices 108 (for example, but not limited to, medical devices 108-1, 108-2, 108-3, 108-4, . . . 108-*n*), and a database 110. In some embodiments, communication between the server 102, the one or more imaging devices 104, the one or more user devices 106, the one or more medical devices 108, and the database 110 occur through a network 112. In some embodiments, the network 112** is, for example, a wide area network (WAN) (for example, a transport control protocol/internet protocol (TCP/IP) based network), a cellular network, or a local area network (LAN) employing any of a variety of communications protocols as is well known in the art or developed in the future.

The components and the functionality of the one or more imaging devices 104 are now described in detail. For ease of reference, the components, and the functionality of one imaging device 104 are described hereinafter, however each of the same components and functionality are applicable to other imaging devices 104 shown in FIG. 1. In accordance with various embodiments, the imaging device 104 is configured to capture a plurality of video frames associated with execution of one or more medical procedures in a medical procedure room. Each video frame captures one or more first parameters associated with one or more medical items and one or more second parameters associated with one or more medical practitioners during each medical procedure. The imaging device 104 is any device capable of capturing video frames including continuous images or sequential still images of the one or more medical items, the one or more medical practitioners, and the medical procedure room. For example, the imaging device 104 includes one or more of a low-angle camera 104-1, a wall-mounted camera 104-2, an augmented reality device **104-*n*, or any device, now known or in the future developed, which can capture video frames and/or record or generate videos of the one or more medical items, the one or more medical practitioners, and the medical procedure room. The imaging device 104 transmits the video frames to the server 102 and/or the database 110**.

Figure 4:
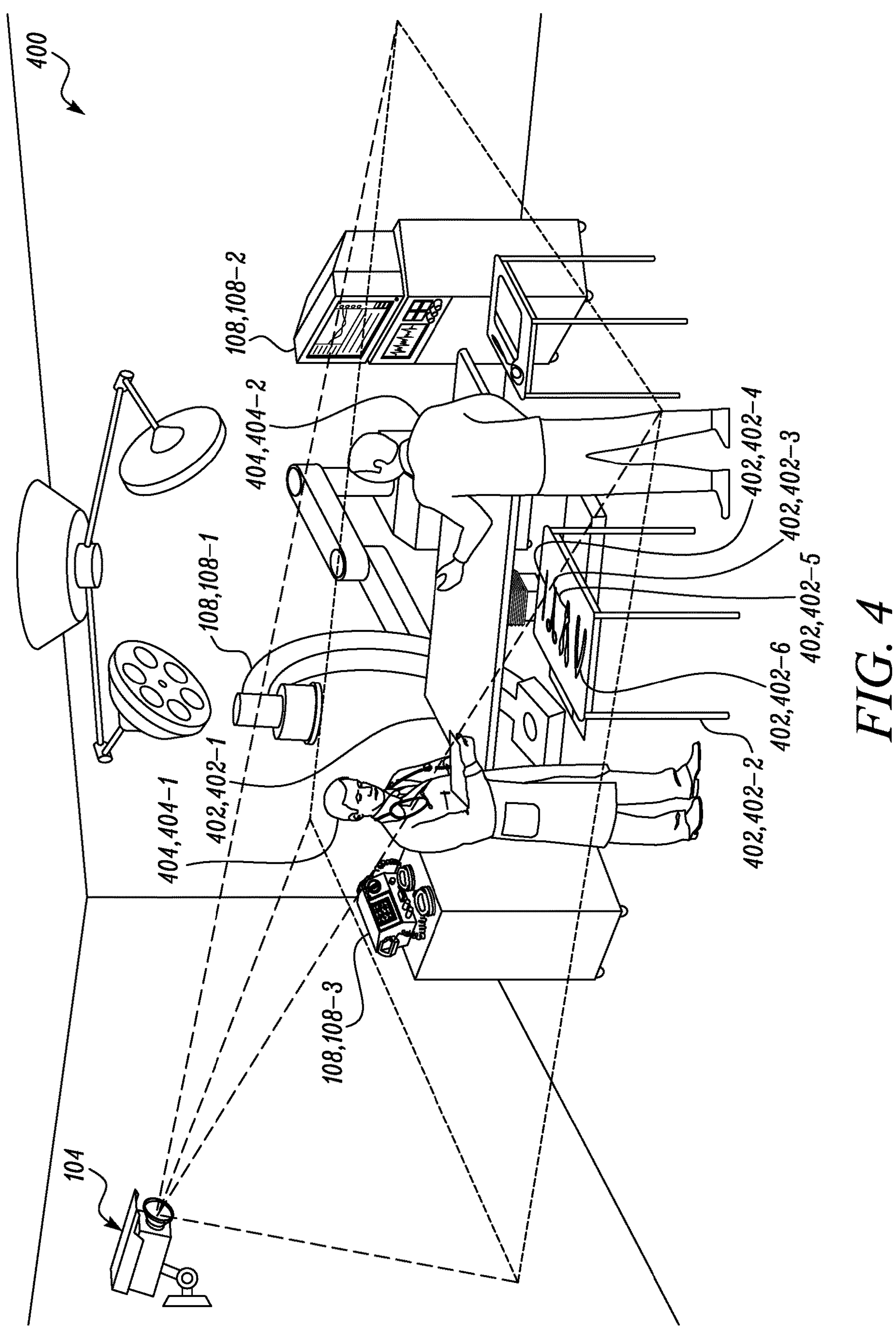
FIG. 4 illustrates an imaging device installed in a medical procedure room for capturing video frames associated with an execution of the medical procedure, in accordance with some embodiments.

In accordance with various embodiments, the imaging devices 104 are installed in each medical procedure room of the one or more medical procedure rooms for capturing the video frames associated with the execution of the one or more medical procedures. The medical procedure room is any room that is used by one or more medical practitioners for performing a medical procedure and includes one or more medical items for use during the medical procedure. For example, as shown in FIG. 4, a medical procedure room 400 includes the medical items 402, such as, but not limited to, a medical procedure table 402-1, one or more auxiliary tables 402-2 or stands (such as a Mayo stand), a surgical scissor 402-3, a surgical needle 402-4, a forceps 402-5, a surgical tweezer 402-6, and various other medical items (not shown), now known or in the future developed, for use by one or more medical practitioners 404 (for example, the medical practitioners 404-1 and 404-2) during the medical procedure. It will be understood that the medical procedure room 400 is not limited to the medical items 402 and the medical practitioners 404 shown in FIG. 4 and includes any number of medical items and the medical practitioners. Each imaging device 104 can be configured to capture one or more first parameters for each medical item 402 and one or more second parameters associated with each medical practitioner 404. For example, in one embodiment, the one or more first parameters associated with the medical item 402 include one or more of a movement and time stamps associated with the movement of the corresponding medical item 402 and a positioning and time stamps associated with the positioning of the corresponding medical item 402. Further for example, in one embodiment, the one or more second parameters for each medical practitioner 404 include one or more of a movement and time stamps associated with the movement of the corresponding medical practitioner 404 and a positioning and time stamps associated with the positioning of the corresponding medical practitioner 404. It will be appreciated that the one or more first and second parameters can be any parameter associated with the medical procedure now known or in the future developed.

In some embodiments, the medical procedure room also includes one or more medical devices 108, such as, anesthesia systems, electrocautery systems, C-arm systems, enabling technology systems or workstations (for example, but not limited to, a microscope, an electrocardiogram device, a robotic surgical system, a navigation system, a networked robotics, an illumination system, or any other enabling technology systems now known or in the future developed, and accompanying monitors or displays), a blood pressure monitoring machine, a heart rate monitoring machine, and various other medical devices (not shown) now known or in the future developed. For example, as shown in FIG. 4, the medical procedure room 400 includes the medical devices 108, such as, but not limited to, a C-arm system 108-1, an anesthesia system 108-2, and a defibrillator 108-3. In accordance with various embodiments, one or more outputs of the medical devices 108 are provided to the server 102 and/or the database 110.

Referring back to FIG. 1, the database 110 stores the plurality of video frames associated with the one or more medical procedures. The plurality of video frames are associated with a medical procedure identifier identifying the type of medical procedure. In an exemplary embodiment, the plurality of video frames are further associated with one or more medical practitioner identifiers identifying the medical practitioners performing the medical procedure and a medical procedure room identifier identifying the medical procedure room in which the medical procedure is performed. In some embodiments, the database 110 also stores one or more predefined operative report templates and one or more predefined medical reference manual templates for generation of the one or more operative reports and the medical reference manual, respectively. In some embodiments, the database 110 also stores the medical reference manual and the one or more operative reports generated by the server 102.

Figure 2:
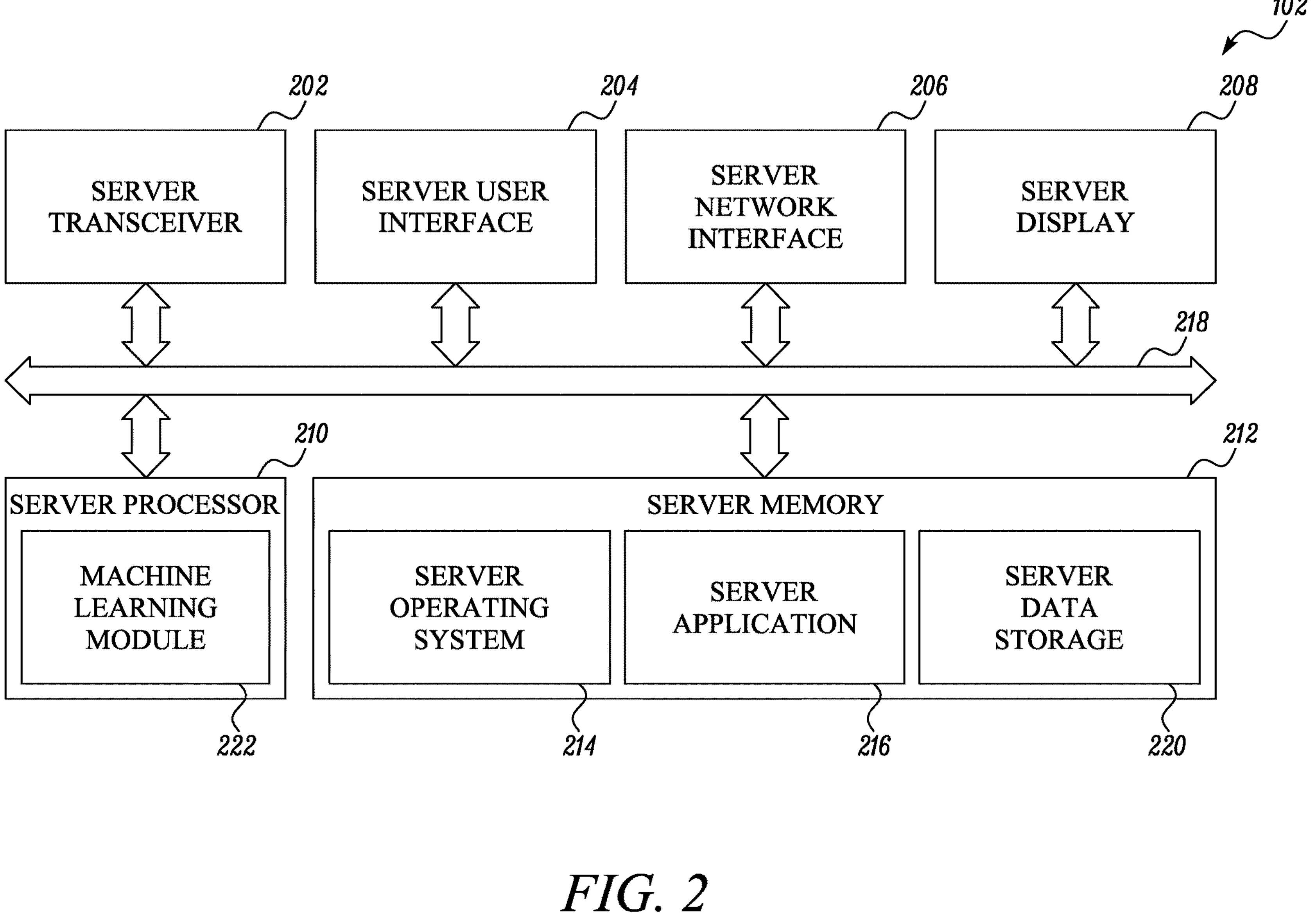
FIG. 2 is a block diagram of a server for use within the system of FIG. 1, in accordance with some embodiments.

The server 102 is configured to generate and continuously optimize the medical reference manual based on the plurality of video frames obtained from the one or more imaging devices 104. For ease of reference, the components and the functionality of the server 102 are described in detail hereinafter with reference to FIGS. 2, 5, and 6. FIG. 2 is a block diagram of one exemplary embodiment of the server 102 for use within the system 100 of FIG. 1 in accordance with some embodiments. The server 102 is electrically and/or communicatively coupled to the one or more imaging devices 104, the one or more user devices 106, the one or more medical devices 108, and the database 110. In some embodiments, the server 102 includes a plurality of electrical and electronic components, for example, for providing power, operational control, and communication within the server 102. For example, in one embodiment, the server 102 includes, among other things, a server transceiver 202, a server user interface 204, a server network interface 206, a server display 208, a server processor 210, and a server memory 212.

It should be appreciated by those of ordinary skill in the art that FIG. 2 depicts the server 102 in a simplified manner and a practical embodiment includes additional components and suitably configured logic to support known or conventional operating features that are not described in detail herein. It will further be appreciated by those of ordinary skill in the art that the server 102 is a personal computer, a desktop computer, a tablet, an augmented reality device, a smartphone, a wearable device (wrist worn, eye worn), or any other server now known or in the future developed. It will further be appreciated by those of ordinary skill in the art that the server 102 alternatively functions within a remote server, a cloud server, or any other remote computing mechanism now known or in the future developed. Although the description below discusses the functions and operations performed by the server 102, a person skilled in the art would appreciate that, in some embodiments, the functions and operations of the server 102 can be performed in a single device or in a distributed manner by two or more devices without limiting the scope of the claimed subject matter.

The components of the server 102 (for example 202, 204, 206, 208, 210, and 212) are communicatively coupled via a server local interface 218. The server local interface 218 includes, for example, but not limited to, one or more buses or other wired or wireless connections, as is now known in the art or in the future developed. In an embodiment, the server local interface 218 has additional elements, which are omitted for simplicity, such as controllers, buffers (caches), drivers, repeaters, and receivers, among many others, to enable communications. Further, in some embodiments, the server local interface 218 includes address, control, and/or data connections to enable appropriate communications among the aforementioned components.

The server 102 in the illustrated example includes the server transceiver 202. The server transceiver 202, incorporating a server transceiver antenna (not shown), enables wireless communication between the server 102 and other devices, (for example, the one or more imaging devices 104, the one or more user devices 106, the one or more medical devices 108, and the database 110). It will be appreciated by those of ordinary skill in the art that the server 102 includes a single server transceiver 202 as shown, or alternatively separate transmitting and receiving components, for example, but not limited to, a transmitter, a transmitting antenna, a receiver, and a receiving antenna and/or any combination thereof.

The server user interface 204 is used to receive one or more user inputs from and/or for providing one or more system outputs from/to the user (for example, a medical procedure room personnel, a surgical resident, a medical student, a trainee or any other medical practitioner) or from/to the one or more user devices 106. User input is provided via, for example, a keyboard, a touchpad, a mouse, a microphone, an augmented reality device, a camera, a headset, a Light Detection and Ranging (LiDAR) system, and/or any other user input now known or in the future developed, or any combination thereof. System output is provided via a server display 208, a server speaker (not shown), a printer (not shown) and/or any other system output now known or in the future developed, or any combination thereof. The server user interface 204 further includes, for example, a serial port, a parallel port, an infrared (IR) interface, a universal serial bus (USB) interface, a Bluetooth® interface, a wireless Fidelity (Wi-Fi) interface, a Near-field communication (NFC) interface, and/or any other interface for wired or wireless communication, now known or in the future developed.

The server network interface 206 is used to enable the server 102 to communicate on a network, such as, the network 112 of FIG. 1, a wireless access network (WAN), and a radio frequency (RF) network. The server network interface 206 includes, for example, an Ethernet card or adapter or a wireless local area network (WLAN) card or adapter. Additionally, or alternatively, the server network interface 206 includes a radio frequency interface for wide area communications, such as Long-Term Evolution (LTE) networks, or any other network now known or in the future developed. In an embodiment, the server network interface 206 includes address, control, and/or data connections to enable appropriate communications on the network. The server display 208 includes a display screen, a projector, a monitor or any other visual output device now known or in the future developed. In accordance with some embodiments, the server display 208 is configured to display any data, images, or information, such as, the medical reference manual and the operative reports.

The server memory 212 includes any non-transitory memory elements comprising one or more of volatile memory elements (for example, a random access memory (RAM), nonvolatile memory elements (for example, read-only memory "ROM"), and combinations thereof). Moreover, the server memory 212 incorporates electronic, magnetic, optical, and/or other types of storage media now known or in the future developed. Note that, in some embodiments, the server memory 212 has a distributed architecture, where various components are situated remotely from one another, but are accessed by the server processor 210. The software in the server memory 212 includes one or more software programs, each of which includes an ordered listing of executable instructions for implementing logical functions. The software in the server memory 212 includes a server operating system 214 and one or more server applications 216. The server operating system 214 controls the execution of other computer programs, such as, the one or more server applications 216, and provides scheduling, input-output control, file and data management, memory management, and communication control and related services. The one or more server applications 216 are configured to implement the various processes, algorithms, methods, techniques described herein. In accordance with various embodiments, the one or more server applications 216 includes an image processing software to process and analyze the plurality of video frames obtained from the one or more imaging devices 104 to identify the one or more medical items, the one or more medical practitioners, and the medical procedure room in the plurality of video frames and determine the one or more first parameters and the one or more second parameters. A person skilled in the art would appreciate that the image processing software can include a software that is capable of processing the plurality of video frames to identify the one or more medical items, the one or more medical practitioners, and the medical procedure room in the plurality of video frames and further determine the one or more first parameters associated with the one or more medical items and the one or more second parameters associated with the one or more medical practitioners.

The server memory 212 further includes a server data storage 220 used to store data. In the exemplary embodiment of FIG. 2, the server data storage 220 is located internal to the server memory 212 of the server 102. Additionally, or alternatively (not shown), the server data storage 220 is located external to the server 102 such as, for example, an external hard drive connected to the server user interface 204. In some embodiments (not shown), the server data storage 220 is located external and connected to the server 102 through a network and accessed via the server network interface 206. In some embodiments, the externally located server data storage 220 corresponds to the database 110 that stores one or more of the plurality of video frames, the one or more predefined operative report templates, the one or more predefined medical reference manual templates, the one or more medical reference manuals, and the one or more operative reports. Alternatively, in other embodiments, the server data storage 220 and the database 110 are distinct independent storage units. In such cases, the data associated with the plurality of video frames, the one or more predefined operative report templates, the one or more predefined medical reference manual templates, the one or more medical reference manuals, and the one or more operative reports is stored either in the server data storage 220 or the database 110 or in a distributed manner in both the server data storage 220 and the database 110.

The server processor 210 is a hardware device for executing software instructions. In an embodiment, the server processor 210 is any custom made or commercially available processor, a central processing unit (CPU), an auxiliary processor among several processors associated with the server processor 210, a semiconductor-based microprocessor, or generally any device for executing software instructions now known or in the future developed. When the server 102 is in operation, the server processor 210 is configured to execute software stored within the server memory 212, to communicate data to and from the server memory 212, and to generally control operations of the server 102 pursuant to the software instructions.

The server processor 210 includes a machine learning module 222 having a machine learning model configured to optimize the steps in the medical reference manual. The optimization performed by the machine learning module 222 is static or dynamic in nature depending upon the preference of the user. The machine learning module 222 is configured to learn and adapt itself to continuous improvement in changing environments. The machine learning module 222 employs any one or combination of the following computational techniques: neural network, constraint program, fuzzy logic, classification, conventional artificial intelligence, symbolic manipulation, fuzzy set theory, evolutionary computation, cybernetics, data mining, approximate reasoning, derivative-free optimization, decision trees, and/or soft computing. The machine learning module 222 implements an iterative learning process. The learning is based on a wide variety of learning rules or training algorithms now known or in the future developed. In an embodiment, the learning rules include, for example, one or more of back-propagation, pattern-by-pattern learning, supervised learning, and/or interpolation. The machine learning module 222 is configured to implement one or more machine learning algorithms to continuously optimize each of the medical reference manuals. In accordance with some embodiments of the invention, the machine learning algorithm utilizes any machine learning methodology, now known or in the future developed, for classification. For example, the machine learning methodology utilized includes one or a combination of: Linear Classifiers (Logistic Regression, Naive Bayes Classifier); Nearest Neighbor; Support Vector Machines; Decision Trees; Boosted Trees; Random Forest; and/or Neural Networks. The machine learning module 222 continually evolves specifics associated with steps included in the medical reference manual in real time with new data inputs. The machine learning intent is to continually optimize the steps included in the medical reference manual.

In some embodiments, each of the one or more user devices 106 operates as a user interface for one or more users, such as, the medical practitioners, for viewing and/or referring to one or more medical reference manuals and the one or more operative reports generated by the server 102. For ease of reference, the components, and the functionality of one user device 106 are described hereinafter, however each of the same components and functionality are applicable to other user devices 106 shown in FIG. 1.

Figure 3:
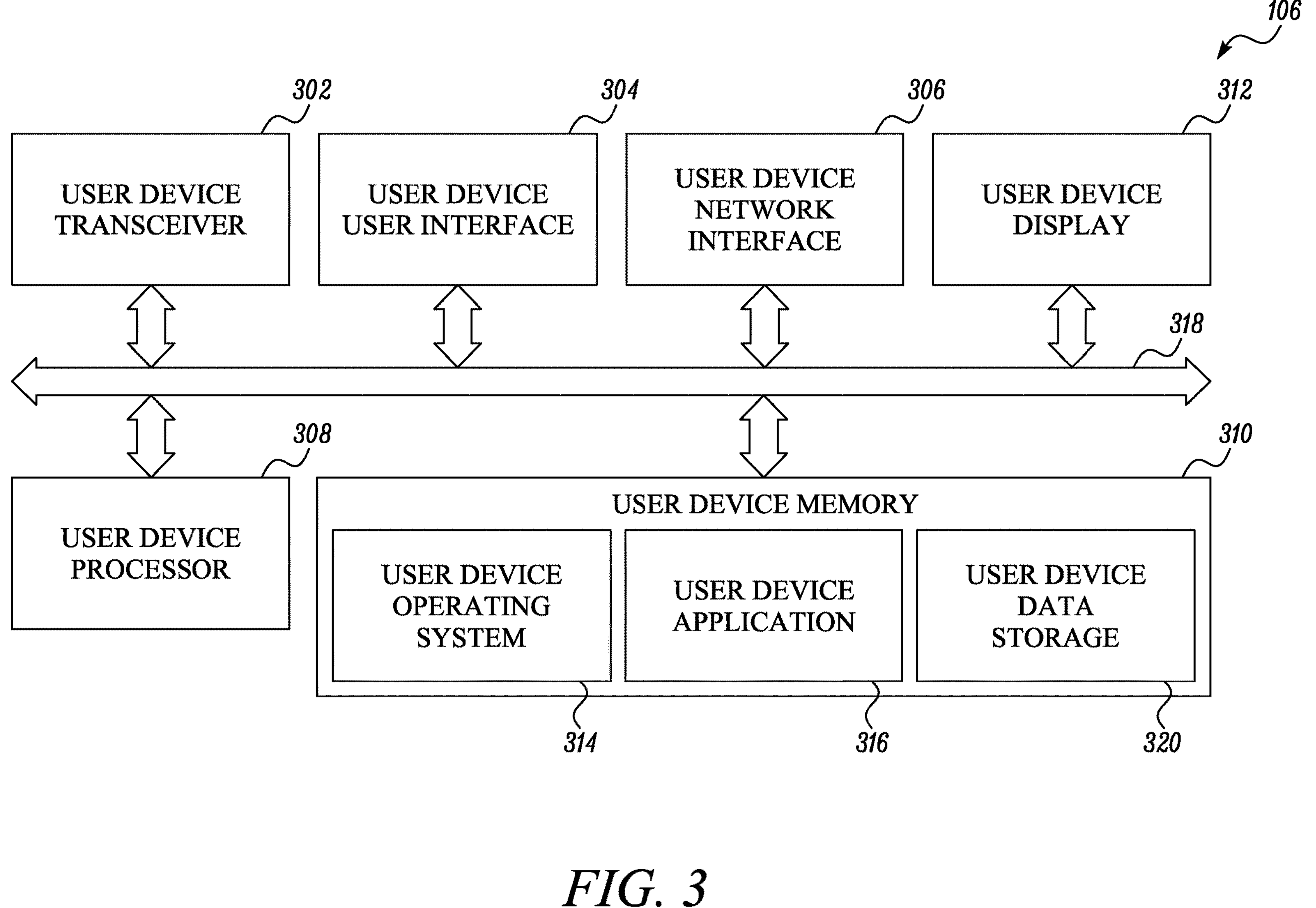
FIG. 3 is a block diagram of a user device for use within the system of FIG. 1, in accordance with some embodiments.

FIG. 3 is a block diagram of one exemplary embodiment of the user device 106 for use within the system 100 of FIG. 1. In accordance with some embodiments, the user device 106 is a tablet 106-1, a smartphone 106-2, an augmented reality or wearable device 106-*n*, or any other user device now known or in the future developed. In some embodiments, the user device 106 is electrically and/or communicatively coupled to a variety of other devices, for example, the server 102 and the database 110. The user device 106 includes a number of electrical and electronic components, providing power, operational control, communication within the user device 106. For example, the user device 106 in one embodiment includes, among other elements, a user device transceiver 302, a user device user interface 304, a user device network interface 306, a user device processor 308, a user device memory 310, and a user device display 312. Although the description below discusses the functions and operations performed by the user device 106, a person skilled in the art would appreciate that, in some embodiments, the functions and operations of the user device 106 can be performed in a single device or in a distributed manner by two or more devices without limiting the scope of the claimed subject matter.

The components of the user device 106 (for example 302, 304, 306, 308, 310, 312) are communicatively coupled via a user device local interface 318. The user device local interface 318 includes, for example, but is not limited to, one or more buses or other wired or wireless connections, as is now known in the art or in the future developed. In an embodiment, the user device local interface 318 has additional elements, which are omitted for simplicity, such as controllers, buffers (caches), drivers, repeaters, and receivers, among many others, to enable communications. Further, in some embodiments, the user device local interface 318 includes address, control, and/or data connections to enable appropriate communications among the aforementioned components.

The user device 106 includes the user device transceiver 302. The user device transceiver 302 incorporating a user device transceiver antenna (not shown), enables wireless communication between the devices, for example, the server 102 and the database 110 of FIG. 1. It will be appreciated by those of ordinary skill in the art that the user device 106 includes a single user device transceiver 302 as shown, or alternatively separate transmitting and receiving components, for example but not limited to, a transmitter, a transmitting antenna, a receiver, and a receiving antenna and/or any combination thereof.

The user device user interface 304 is used to receive input from the server 102 and the database 110 and/or for providing system output from/to the user (for example, the medical practitioners) or from/to the one or more devices. The user device user interface 304 includes one or more input devices, including but not limited to a navigation key, a function key, a microphone, an augmented reality device, a camera, a headset, a Light Detection and Ranging (LiDAR) system, a voice recognition component, a joystick, or any other mechanism capable of receiving an input from a user now known or in the future developed, or any combination thereof. Further, the user device user interface 304 includes one or more output devices, including but not limited to a speaker, headphones, a display, or any other mechanism capable of presenting an output to a user now known or in the future developed, or any combination thereof. In some embodiments, the user device user interface 304 includes a user interface mechanism, such as a touch interface or gesture detection mechanism that allows a user to interact with the displayed output. The user device display 312 is a separate user interface or combined within the user device user interface 304 for displaying information such as the medical reference manual or the one or more operative reports received from the server 102 via the network 112 of FIG. 1.

The user device network interface 306 is used to enable the user device 106 to communicate on a network, such as, the network 112 of FIG. 1, a wireless access network (WAN), and a radio frequency (RF) network. In an embodiment, the user device network interface 306 includes, for example, an Ethernet card or adapter or a wireless local area network (WLAN) card or adapter. Additionally, or alternatively, the user device network interface 306 includes a radio frequency interface for wide area communications such as Long-Term Evolution (LTE) networks, or any other network now known or in the future developed. In some embodiments, the user device network interface 306 includes address, control, and/or data connections to enable appropriate communications on the network.

The user device memory 310 includes any non-transitory memory elements comprising one or more of volatile memory elements (for example, a random access memory (RAM), nonvolatile memory elements (for example, read-only memory "ROM"), and combinations thereof). Moreover, in some embodiments, the user device memory 310 incorporates electronic, magnetic, optical, and/or other types of storage media now known or in the future developed. Note that, in an embodiment, the user device memory 310 has a distributed architecture, where various components are situated remotely from one another but are accessed by the user device processor 308. The software in the user device memory 310 includes one or more software programs, each of which includes an ordered listing of executable instructions for implementing logical functions. The software in the user device memory 310 includes a suitable user device operating system 314 and one or more user device applications 316. The user device operating system 314 controls the execution of other computer programs, such as, the one or more user device applications 316, and provides scheduling, input-output control, file and data management, memory management, and communication control and related services. The one or more user device applications 316 are configured to implement the various processes, algorithms, methods, techniques described herein.

The user device memory 310 further includes a user device data storage 320 used to store data. In the exemplary embodiment of FIG. 3, the user device data storage 320 is located internal to the user device memory 310 of the user device 106. Additionally, or alternatively, the user device data storage 320 are located external to the user device 106 such as, for example, an external hard drive connected to the user device user interface 304 (not shown). In a further embodiment, the user device data storage 320 are located external and connected to the user device 106 through a network and accessed via the user device network interface 306 (not shown).

In operation, information for storage, such as the inputs to update the medical reference manual or the operative reports in the user device data storage 320 is entered via the user device user interface 304. Alternatively, information, for example, the medical reference manual and the operative reports for storage in the user device data storage 320 is received from the server 102 via the user device transceiver 302. In some embodiments, the data stored in the user device data storage 320, for example, the inputs, is further provided to the database 110 and/or the server 102 for updating the medical reference manual and the operative reports stored in the database 110 and/or the server 102.

The user device processor 308 is a hardware device for executing software instructions now known or in the future developed. In an embodiment, the user device processor 308 is any custom-made or commercially available processor, a central processing unit (CPU), an auxiliary processor among several processors associated with the user device processor 308, a semiconductor-based microprocessor, or generally any device for executing software instructions. When the user device 106 is in operation, the user device processor 308 is configured to execute software stored within the user device memory 310, to communicate data to and from the user device memory 310, and to generally control operations of the user device 106 pursuant to the software instructions. The detailed functionalities and operations of the user device processor 308 will be described hereinafter in greater detail.

The description below discusses the functions and operations performed by the respective server 102, imaging device 104, user device 106, and medical device 108. Although the description below discusses the functions and operations performed by the respective server 102, imaging device 104, user device 106, and medical device 108, a person skilled in the art would appreciate that, in some embodiments, the functions and operations of the server 102, the imaging device 104, the user device 106, and the medical device 108 are performed in a single device or in a distributed manner by two or more devices without limiting the scope of the claimed subject matter.

Figure 5A:
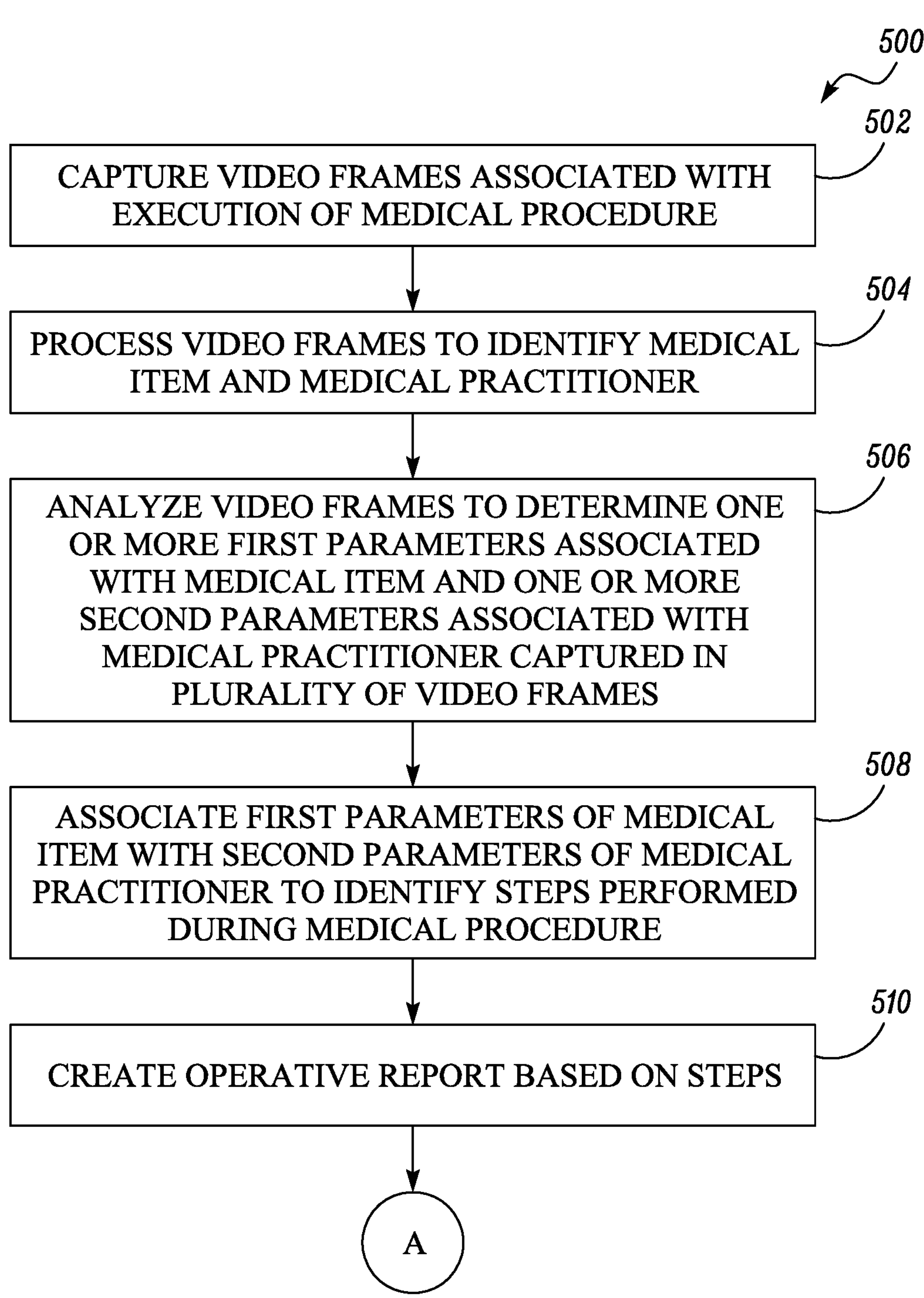
FIGS. 5A and 5B depict a flow diagram of a method for continuously optimizing the medical reference manual for the type of medical procedure, in accordance with some embodiments.
Figure 5B:
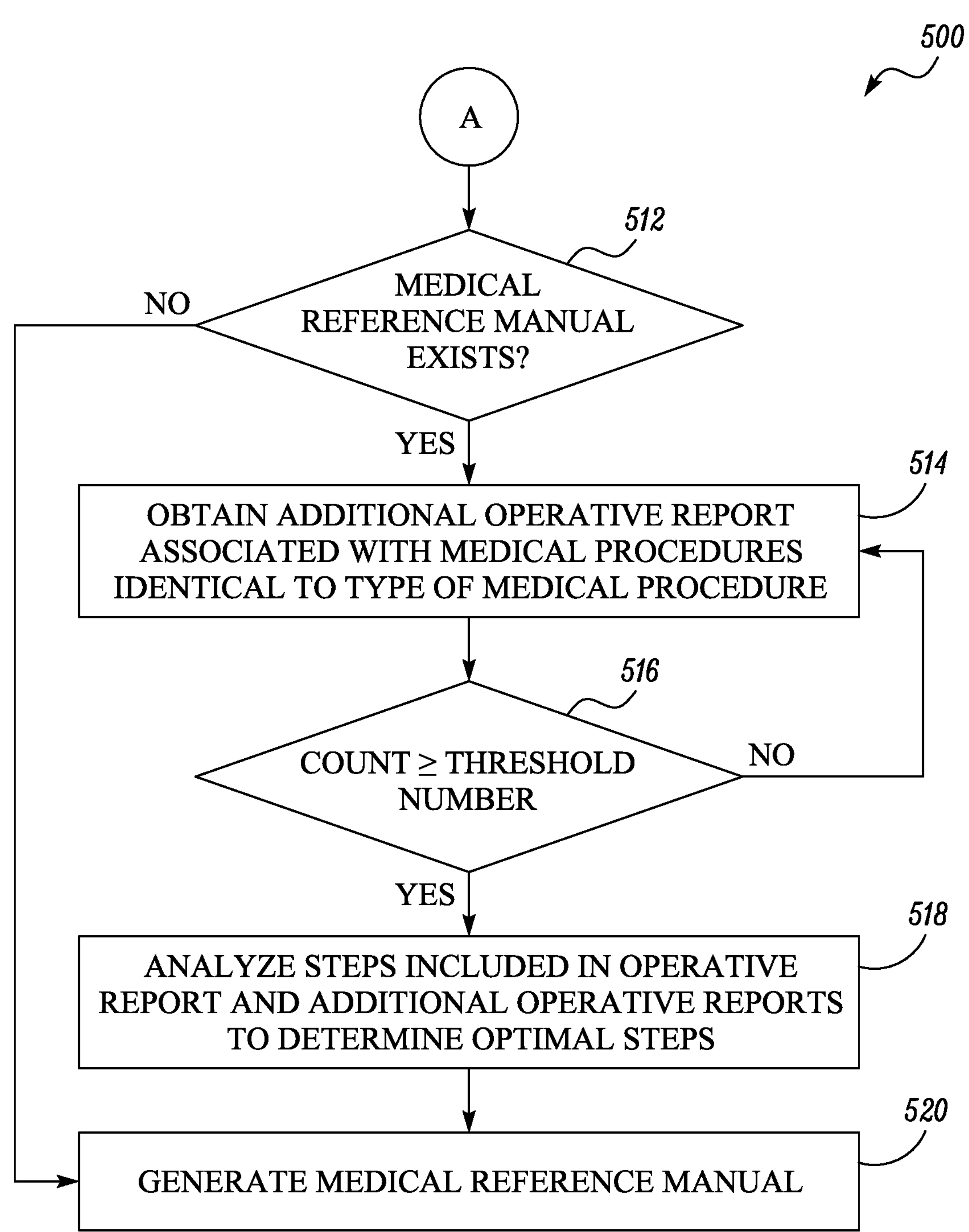

FIGS. 5A and 5B depict a flow diagram of a method 500 for generating and optimizing the medical reference manual for a type of a medical procedure. For ease of reference, the method for generating and optimizing the medical reference manual is described for one type of a medical procedure, however the method can be utilized to generate and optimize the medical reference manual for each type of the one or more type of the medical procedures.

The method 500 begins at 502, with the one or more imaging devices 104 capturing the plurality of video frames associated with execution of the type of medical procedure and transmitting the plurality of video frames to the server 102. At 504, the server processor 210 of the server 102 processes the plurality of video frames to identify the one or more medical items (for example, the medical items 402 shown in FIG. 4), the one or more medical practitioners (for example, the medical practitioners 404 shown in FIG. 4), and the medical procedure room (for example, the medical procedure room 400 shown in FIG. 4) in the plurality of video frames. In accordance with various embodiments, the server processor 210 of the server 102 utilizes the image processing software to identify the one or more medical items, the one or more medical practitioners, and the medical procedure room in the plurality of video frames. For example, the image processing software when executed by the server processor 210 identifies the one or more medical items, the one or more medical practitioners, and the medical procedure room by comparing the captured images of the respective one or more medical items, the one or more medical practitioners, and the medical procedure room with images stored in one or more online image libraries. The server processor 210 of the server 102 then displays one or more medical item identifiers identifying the respective one or more medical items, one or more medical practitioner identifiers identifying the respective one or more medical practitioners, and a medical procedure room identifier identifying the medical procedure room on the server display 208 or the user device display 312 for verification by the user. In some embodiments, the server processor 210 upon receiving an indication from the user that the displayed identification is not verified, enables the user to provide the one or more medical item identifiers identifying the respective one or more medical items, the one or more medical practitioner identifiers identifying the respective one or more medical practitioners, and the medical procedure room identifier identifying the medical procedure room via the server user interface 204 or the user device user interface 304. In some embodiments, for example, when a medical item, a medical practitioner, or the medical procedure room is not identified or verified, the server processor 210 of the server 102 prompts the user (for example, the one or more medical practitioners 404) to enter the medical item identifier and/or the medical practitioner identifier and/or the medical procedure room identifier of the respective unidentified medical item and/or the medical practitioner and/or the medical procedure room via the server user interface 204 or the user device user interface 304. In some embodiments, the machine learning module 222 of the server 102 continuously updates the medical item identifier and/or the medical practitioner identifier and/or the medical procedure room identifier based on inputs, such as, the indication, the one or more medical item identifiers, the one or more medical practitioner identifiers, and the medical procedure room identifier received from the user.

At 506, the server processor 210 of the server 102 analyzes the plurality of video frames to determine the one or more first parameters associated with each of the one or more medical item (for example, the medical items 402 shown in FIG. 4) and the one or more second parameters associated with each of the one or more medical practitioners (for example, the medical practitioners 404 shown in FIG. 4) captured in the plurality of video frames. For example, the one or more first parameters for each medical item 402 include one or more of a movement and time stamps associated with the movement of the corresponding medical item 402 and a positioning and time stamps associated with the positioning of the corresponding medical item 402. The one or more second parameters for each medical practitioner 404 include one or more of a movement and time stamps associated with the movement of the corresponding medical practitioner 404 and a positioning and time stamps associated with the positioning of the corresponding medical practitioner 404. For example, the server processor 210 upon identifying the medical item, such as, an incision device, at 504, obtains the one or more first parameters, such as, a movement and time stamps associated with the movement of the incision device and/or a positioning and time stamps associated with the positioning of the incision device at 506.

At 508, the server processor 210 of the server 102 associates the one or more first parameters of the medical item with the one or more second parameters of the medical practitioner to identify one or more steps performed during the medical procedure. For example, the server processor 210 determines a step to be an incision process when the server processor 210 determines that the incision device was moved by the medical practitioner from X position that represents positioning of the incision device on an auxiliary table 402-2 to Y position that represents positioning of the incision device closer to the medical procedure table 402-1 for Z minutes. In some embodiments, the server processor 210 also determines, based on the association, whether the medical procedure is a left side medical procedure or a right side medical procedure.

At 510, the server processor 210 of the server 102 creates an operative report for the medical procedure based on the identified one or more steps performed during the medical procedure. In accordance with various embodiments, the server 102 indicates the identified one or more steps performed during the medical procedure in a descriptive manner in the operative report. In some embodiments, the server processor 210 of the server 102 indicates the one or more steps in the one or more predefined operative report templates to create the operative report. For example, the operative report includes the identified incision step and also indicates the time period (for example, Z minutes) for which the incision step was performed.

In some embodiments, the server processor 210 receives one or more inputs such as, the medical procedure identifier that corresponds to the medical procedure performed, the medical practitioner identifier that corresponds to a medical practitioner performing the medical procedure, and the medical procedure room identifier that corresponds to the medical room in which the medical procedure is performed, from the medical practitioner and associates the one or more inputs with the operative report. For example, when the medical procedure corresponds to a spinal surgery, the medical procedure identifier, such as, for a spinal surgery, is associated with the operative report. In cases where two or more medical practitioners are performing the medical procedure, the server processor 210 is configured to associate the medical practitioner identifiers of each of the two or more medical practitioners with the operative report.

In some embodiments, the server processor 210 of the server 102 updates the operative report associated with the medical procedure based on one or more user inputs. In such cases, the server processor 210 of the server 102 displays the created operative report on the server display 208 and receives one or more user inputs from the user (for example, the one or more medical practitioners 404) to modify the displayed operative report via the server user interface 204. In some embodiments, the server processor 210 of the server 102 transmits the created operative report to the user device 106 and instructs the user device 106 to display the created operative report on the user device display 312 and receives one or more user inputs from the user via the user device user interface 304. In such cases, the user device 106 transmits the one or more user inputs to the server 102, for example, via the user device transceiver 302, for updating the operative report based on the one or more user inputs. For example, the one or more user inputs include, but not limited to, an addition of a step, a change in sequence of the identified one or more steps, or an addition of descriptive text to the one or more steps indicated in the operative report.

In some embodiments, the server processor 210 of the server 102 obtains, via the server transceiver 202, the one or more outputs from the one or more medical devices 108 associated with the medical procedure and modify the operative report based on the one or more outputs. The server processor 210 of the server 102 includes or modifies data associated with the steps included in the operative report based on the one or more outputs from the one or more medical devices 108. For example, the server processor 210 of the server 102 obtains imaging data from the C-arm system 108-1 and includes the imaging data in the operative report. In some embodiments, the server processor 210 of the server 102 includes one or more processing modules (not shown) that when executed by the server processor 210 analyzes the one or more outputs obtained from the medical devices 108 and provides descriptive data associated with the one or more outputs for insertion in the operative report. For example, in one scenario, the server application 216 of the server 102 includes one or more x-ray image processing modules (not shown) that when executed by the server processor 210 analyzes the imaging data obtained from the C-arm system 108-1 and provides descriptive data associated with the imaging data for insertion in the operative report. The server processor 210 then stores the operative report in the server data storage 220 or the database 110.

At 512, the server processor 210 of the server 102 determines whether the medical reference manual for this type of medical procedure exists. When the server processor 210 determines that the medical reference manual for this type of medical procedure does not exist, the server processor 210 generates the medical reference manual based on the steps indicated in the created operative report at 520. In accordance with various embodiments, the server processor 210 of the server 102 includes the steps of the operative report in a predefined medical reference manual template to generate the medical reference manual.

When the server processor 210, at 512, determines that the medical reference manual for this type of medical procedure exists, the server processor 210, at 514, obtains one or more additional operative reports associated with one or more medical procedures similar or identical to the type of the medical procedure from the server memory 212 or the database 110. In some embodiments, the method 500, upon creation of the operative report at 510, directly proceeds to 514 to obtain the one or more additional operative reports for generation of the medical reference manual depending upon the preference of the user.

For example, when the medical procedure for which the operative report is created is a spinal surgery, the server 102 obtains one or more additional operative reports associated with one or more medical procedures similar or identical to the spinal surgery. The one or more additional operative reports corresponds to one or more medical procedures performed prior to the medical procedure. In some embodiments, the one or more additional operative reports are generated/created by the server processor 210 of the server 102 based on a plurality of video frames captured during execution of the corresponding one or more medical procedures and/or manually entered by one or more users in the server data storage 220 or the database 110. In some embodiments, the one or more additional operative reports are the reports that were previously not considered for the generation of the medical reference manual.

In accordance with various embodiments, the one or more additional operative reports are associated with one or more of a plurality of medical practitioner identifiers identifying a plurality of medical practitioners and/or a plurality of medical procedure room identifiers identifying a plurality of medical procedure rooms. In such cases, the medical reference manual that is generated by the server processor 210 (at 520) is not specific to any medical practitioner and/or any medical procedure room. For example, in this embodiment, when the server processor 210 generates the operative report for a spinal surgery performed by the medical practitioner 'A' in the medical procedure room 'X', the server processor 210 obtains one or more additional operative reports for other spinal surgeries performed by a plurality of medical practitioner and/or in various medical procedure rooms and generates the medical reference manual for performing spinal surgeries that is not specific to any medical practitioner or the medical procedure room.

In some embodiments, the system 100 also generates and continuously optimizes one or more medical reference manuals specific to each of the one or more medical practitioners performing the medical procedure and/or medical procedure room in which the medical procedure is performed based on requirements of the user. To this end, the obtained one or more additional operative reports are associated with one or more of the medical practitioner identifiers identifying the medical practitioners who performed the medical procedure and the medical procedure room identifier identifying the medical procedure room in which the medical procedure is performed. For example, the server processor 210 obtains one or more additional operative reports for other spinal surgeries performed by the medical practitioner 'A' in one or more medical procedure rooms and generates a medical reference manual for performing spinal surgeries that is specific to the medical practitioner 'A'. Alternatively, or additionally, in some cases, the server processor 210 obtains one or more additional operative reports for other spinal surgeries performed by the medical practitioner 'A' in a medical procedure room 'X' and generates a medical reference manual for performing spinal surgeries that is specific to the medical practitioner 'A' and the medical procedure room 'X'.

In some embodiments, the server processor 210, at 516, determines whether a count of operative reports (including the created operative report and the one or more additional operative reports) available for this type of medical procedure is greater than or equal to a threshold number. In accordance with various embodiments, the threshold number is a number defined by the user that corresponds to a minimum number of the operative reports required to generate or update the medical reference manual. When the count of operative reports available for this type of medical procedure is less than the threshold number, the method 500 loops back to 514 to obtain additional operative reports associated with this type of medical procedure.

When the count of operative reports available for this type of medical procedure is greater than or equal to the threshold number, the server processor 210, at 518, analyzes, using the machine learning model of the machine learning module 222, the one or more steps included in the operative report (or interchangeably the medical reference manual, in cases when the method 500 proceeds directly from 512 to 520) and steps included in the one or more additional operative reports to determine optimal steps for the medical procedure. To this end, in some embodiments, the server processor 210 is configured to determine key performance indicators (KPIs) including, but not limited to, one or more of outputs of the one or more medical devices 108, time taken to perform a process/step of the medical procedure, and number/type/model of medical items and/or medical devices 108 used during the execution of the medical procedure and the one or more medical procedures. The server processor 210 further correlates, using the machine learning model, the KPIs with corresponding steps included in the operative report and the one or more additional operative reports and determines, using the machine learning model, the optimal steps for the medical reference manual of the medical procedure based on the correlation.

In some embodiments, the server processor 210 determines the optimal steps based on one or more desired key performance indicators (KPIs) including, but not limited to, one or more of desired outputs of the medical devices 108, desired time taken to perform a process/step of the medical procedure, and usage of desired medical items and/or medical devices 108 to perform the medical procedure. In some embodiments, the optimal steps include averaging out the time taken for performing a process/step of the medical procedure. In some embodiments, the optimal steps are determined based on optimization of one or more steps performed during the medical procedure and the one or more medical procedures that resulted in the desired KPIs using the machine learning model. To this end, the server processor 210 determines KPIs for each medical procedure and data associated with the one or more steps performed during the medical procedure and the one or more medical procedures. The server processor 210 then determines, using the machine learning model, an optimal relationship between the KPIs and the corresponding steps performed during the medical procedure and the one or more medical procedures by analyzing the KPIs and the corresponding steps performed during the medical procedure and the one or more medical procedures. The server processor 210 then determines, using the machine learning model, optimal steps for such type of medical procedures based on the determined relationship. For example, the server processor 210 receives data associated with the desired KPIs for such type of medical procedures from the user and determines the optimal steps for such type of medical procedures based on the determined relationship to obtain the desired KPIs.

For example, the server processor 210 determines and correlates an output of each medical device 108 and data associated with the one or more corresponding steps included in the operative report and the one or more additional operative reports. The server processor 210 then determines, using the machine learning model, an optimal relationship between the output of each medical device 108 and the corresponding steps performed during the medical procedure and the one or more medical procedures by correlating and analyzing the output of each medical device 108 and the corresponding steps performed during the medical procedure and the one or more medical procedures. The server processor 210 then determines, using the machine learning model, optimal steps for such type of medical procedures based on the determined relationship and correlation. For example, the server processor 210 receives data associated with the desired output of the medical device 108 for such type of medical procedures from the user and determines the optimal steps for such type of medical procedures based on the determined relationship to obtain the desired output. For example, the server processor 210 determines one or more outputs of an electrocardiogram device during the medical procedure and the one or more medical procedures and correlates the output with the corresponding one or more steps performed during the medical procedure and the one or more medical procedures. The server processor 210 then determines, using the machine learning model, optimal steps for such type of medical procedures that resulted in desired output of the electrocardiogram device, using the method described above.

In some embodiments, the server processor 210 is configured to determine, using the machine learning model, optimal steps for a phase (for example, a stage) of the medical procedure. In accordance with various embodiments, each medical procedure is divided into a plurality of phases that are to be completed in a sequential manner and the plurality of steps of the medical procedure are divided into one or more sets of steps. For example, a first phase of the medical procedure is a preoperative phase corresponding to a set of steps including usage of one or more medical items, such as, a blood pressure monitor or sphygmomanometer to check the blood pressure, a glucometer to check the blood sugar levels, a temperature monitor to measure the body temperature, and an anesthesia machine for anesthesia. In such cases, the one or more steps of the medical procedure described above correspond to one or more steps of a phase of the medical procedure and the server processor 210, using the method described above, determines optimal steps for one or more phases of the medical procedure.

In some embodiments, the server processor 210 is configured to determine, using the machine learning model, an optimal step corresponding to each step. To this end, the server processor 210, for each step of the medical procedure, obtains one or more KPIs associated with the corresponding step of the medical procedure. The server processor 210 also determines one or more steps of the one or more additional medical procedures corresponding to the step of the medical procedure and obtains the one or more KPIs associated with the determined one or more steps of the one or more additional medical procedures. The server processor 210, then correlates, using the machine learning model, the one or more KPIs associated with the step of the medical procedure and the one or more KPIs associated with the corresponding one or more steps of the one or more additional medical procedures. The server processor 210 then determines, using the machine learning model, the optimal step for the medical reference manual of the medical procedure based on the correlation. To this end, the server processor 210 determines, using the machine learning model, an optimal relationship between the one or more KPIs associated with the step of the medical procedure and the one or more KPIs associated with the corresponding one or more steps of the one or more additional medical procedures by analyzing the one or more KPIs associated with the step of the medical procedure and the one or more KPIs associated with the corresponding one or more steps of the one or more additional medical procedures. The server processor 210 then determines, using the machine learning model, an optimal step corresponding to each step of the medical procedure based on the determined relationship.

In an exemplary embodiment, the server processor 210, for each step of the medical procedure, obtains one or more outputs of one or more medical devices associated with the corresponding step of the medical procedure. The server processor 210 also determines one or more steps of the one or more additional medical procedures corresponding to the step of the medical procedure and obtains the one or more outputs of one or more medical devices 108 associated with the determined one or more steps of the one or more additional medical procedures. The server processor 210, then correlates, using the machine learning model, the one or more outputs of the one or more medical devices 108 associated with the step of the medical procedure and the one or more outputs of the one or more medical devices associated with the corresponding one or more steps of the one or more additional medical procedures. The server processor 210 then determines, using the machine learning model, the optimal step for the medical reference manual of the medical procedure based on the correlation. To this end, the server processor 210 determines, using the machine learning model, an optimal relationship between the one or more outputs of the one or more medical devices 108 associated with the step of the medical procedure and the one or more outputs of the one or more medical devices associated with the corresponding one or more steps of the one or more additional medical procedures by analyzing the one or more outputs of the one or more medical devices 108 associated with the step of the medical procedure and the one or more outputs of the one or more medical devices associated with the corresponding one or more steps of the one or more additional medical procedures. The server processor 210 then determines, using the machine learning model, an optimal step corresponding to each step of the medical procedure based on the determined relationship.

In an exemplary embodiment, the server processor 210 receives data associated with the desired output of the medical device 108 for each step of the medical procedure from the user and determines an optimal step for each step of the medical procedure based on the determined relationship to obtain the desired output. For example, the server processor 210 determines an output of the electrocardiogram device when the spinal cord is decompressed during the spinal surgery and the one or more additional spinal surgeries and correlates the output with the step performed. The server processor 210 then determines, using the machine learning model, an optimal step for decompressing the spinal cord that resulted in desired output of the electrocardiogram device, using the method described above. In some embodiments, when the optimization performed by the machine learning module 222 is static in nature, the server processor 210 proceeds with the generation of the medical reference manual upon determining the optimal steps at 518.

At 520, the server processor 210 of the server 102 generates the medical reference manual based on the determined optimal steps for the medical procedure. In accordance with various embodiments, the server processor 210 of the server 102 indicates the determined optimal steps in a descriptive manner in the medical reference manual. In some embodiments, the server processor 210 of the server 102 includes the determined optimal steps in a predefined medical reference manual template to generate the medical reference manual. In some embodiments, the optimal steps included in the generated medical reference manual depend upon the side of the surgery, for example, the left side surgery or the right side surgery. To this end, the server processor 210 of the server 102 is configured to identify the operative reports and the additional operative reports associated with a particular side of the surgery and then analyze the identified operative report and the additional operative reports to generate the medical reference manual for the particular side of the surgery.

In some embodiments, the server processor 210 updates the optimal steps of the medical reference manual based on one or more user inputs. In such cases, the server processor 210 displays the determined optimal steps on the server display 208 and receives one or more user inputs from the user to modify the optimal step(s) via the server user interface 204. In some embodiments, the server processor 210 transmits the determined optimal steps to the user device 106 via the server transceiver 202 and instructs the user device 106 to display the optimal step(s) on the user device display 312 and receive the one or more user inputs from the user via the user device user interface 304. In such cases, the user device 106 transmits, via the user device transceiver 302, the one or more user inputs to the server processor 210 for updating the optimal steps based on the one or more user inputs. For example, the one or more user inputs include, but not limited to, a change in a technique of performing the optimal step and a change in the order/sequence of performing the optimal step.

In accordance with various embodiments, when the optimization performed by the machine learning module 222 is dynamic, the server processor 210 of the server 102 is configured to continuously obtain subsequent operative reports associated with one or more subsequent medical procedures identical to the type of the medical procedure and analyze the optimal steps included in the medical reference manual and steps included in the subsequent operative reports to update the optimal steps using the machine learning model. The server processor 210 then continuously optimizes the medical reference manual by modifying the medical reference manual based on the updated optimal steps for the medical procedure. The continuous optimization of the medical reference manual is described herein with reference to FIG. 6.

Figure 6:
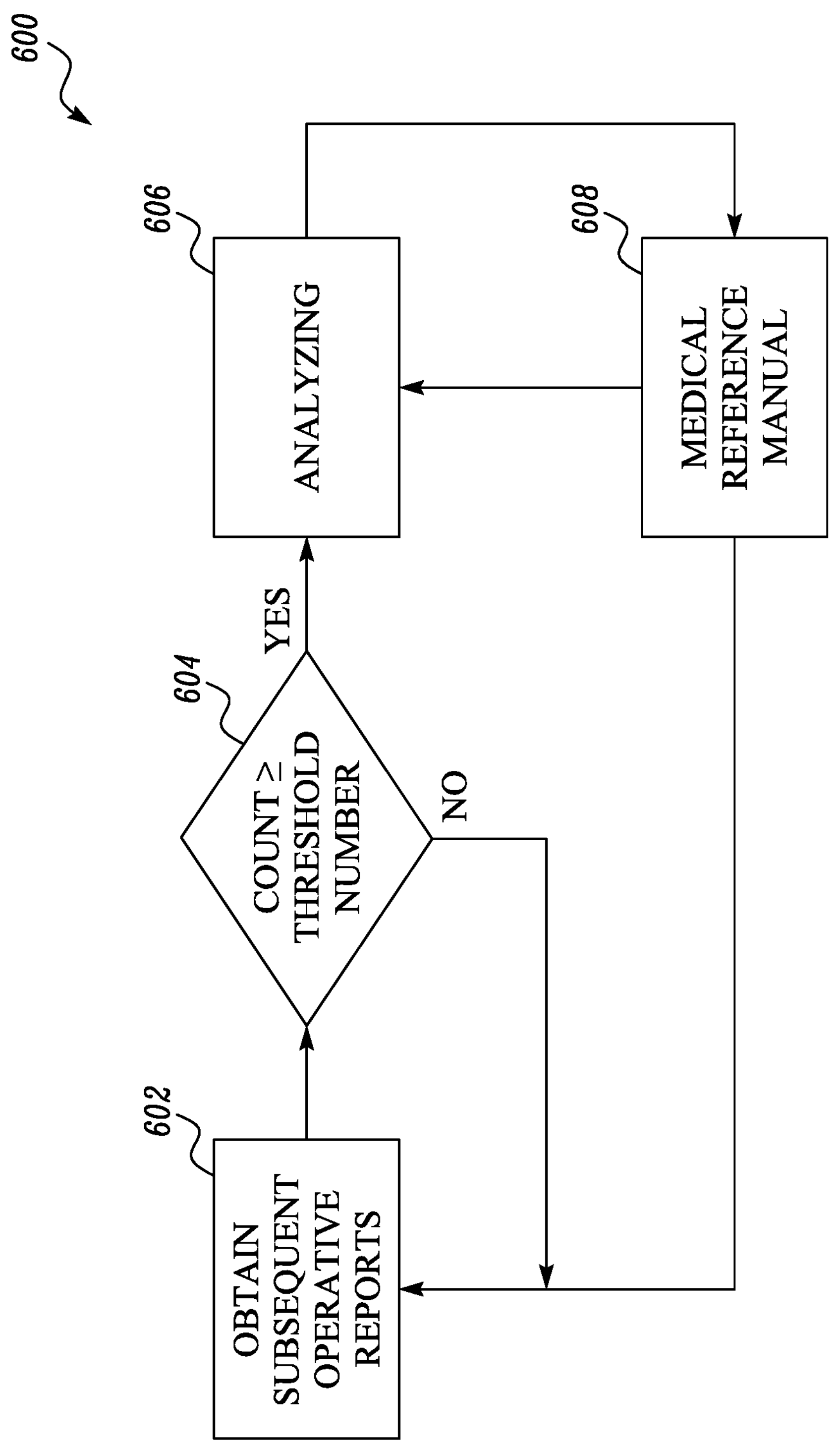
FIG. 6 is a block diagram of an optimization cycle for optimizing the medical reference manual within the server, in accordance with some embodiments.

Referring to FIG. 6, the optimization cycle 600 associated with the optimizing of the medical reference manual is described. At 602, the server 102 (for example, the server processor 210) obtains subsequent operative reports associated with one or more subsequent medical procedures identical to the type of the medical procedure, for example, from the server data storage 220 or the database 110. In some embodiments, the subsequent operative reports correspond to one or more medical procedures performed subsequent to the medical procedure and include reports that were previously not considered for the generation of the medical reference manual. Upon receiving the subsequent operative reports, the server processor 210 determines, at 604, whether a count of the subsequent operative reports is greater than or equal to the threshold number. When the count of the subsequent operative reports is less than the threshold number, the optimization cycle loops back to 602 to obtain more subsequent operative reports associated with one or more subsequent medical procedures identical to the type of the medical procedure. When the count of the subsequent operative reports is equal to or greater than the threshold number, the server processor 210 analyzes, at 606, the subsequent operative reports and the medical reference manual to modify the medical reference manual at 608. In accordance with various embodiments, the server processor 210, at 606, analyzes, using the machine learning model, the optimal steps included in the medical reference manual and steps included in the subsequent operative reports to update the optimal steps and modify the medical reference manual based on the updated optimal steps for the medical procedure at 608.

To this end, as discussed above, the server processor 210 updates, using the machine learning model, the optimal relationship previously determined by the server processor 210 based on the desired KPIs with corresponding steps included in the subsequent operative reports. The server processor 210 then determines, using the machine learning model, updated optimal steps corresponding to the medical procedure for the medical reference manual based on the updated optimal relationship at 608. Upon modifying the medical reference manual, the optimization cycle 600 loops back to 602 to obtain more subsequent operative reports associated with one or more subsequent medical procedures identical to the type of the medical procedure.

In some embodiments, the one or more subsequent operative reports are associated with the medical practitioner identifier identifying the medical practitioner who performed the medical procedure and/or the medical procedure room identifier identifying the medical procedure room in which the medical procedure is performed. In such cases, the medical reference manual that is created by the server processor 210 of the server 102 is specific to the medical practitioner who performed the medical procedure and/or the medical procedure room in which the medical procedure is performed. In some embodiments, the one or more subsequent operative reports are associated with one or more of a plurality of medical practitioner identifiers identifying medical practitioners and/or a plurality of medical procedure room identifiers identifying medical procedure rooms. In such cases, the medical reference manual that is created by the server processor 210 of the server 102 is not specific to any medical practitioner and/or any medical procedure room.

The system and the method of the present disclosure are directed towards generating and continuously optimizing the medical reference manual for assisting the doctors, medical practitioners, surgical residents, medical students, trainees, and/or the like, for performing the medical procedures. By capturing and analyzing the plurality of video frames associated with the execution of the medical procedures, the operative reports can be generated automatically in real time. Further, the system and the method of the present disclosure allow a plurality of operative reports to be considered for generation of the medical reference manual. Moreover, the machine learning model allows continuous optimization of the medical reference manual by analyzing subsequent operative reports associated with the medical procedure with greater speed and accuracy.

The operative reports and the medical reference manual generated by the system and the method of the present disclosure captures every minute detail regarding the execution of the medical procedure. For example, by employing the system and the method of the present disclosure, it is possible to determine an angle at which a particular medical item is being used (interchangeably referred to as the working angle). Such detailed information can be used by the medical practitioner to optimize the medical procedures by determining an optimized working angle for the medical item as well as by the medical companies to design medical items based on the optimized working angle of the medical items.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover, in this document, relational terms such as first and second, top and bottom, and the like may be used solely to distinguish one entity or action from another entity or action without necessarily requiring or implying any actual such relationship or order between such entities or actions. The terms “comprises,” “comprising,” “has”, “having,”

"includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element preceded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way but may also be configured in ways that are not listed.

It will be appreciated that some embodiments may be comprised of one or more generic or specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

Moreover, an embodiment can be implemented as a computer-readable storage medium having computer readable code stored thereon for programming a computer (for example, comprising a processor) to perform a method as described and claimed herein. Examples of such computer-readable storage mediums include, but are not limited to, a hard disk, a CD-ROM, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

The invention claimed is:

1. A system for continuously optimizing a medical reference manual for a medical procedure performed by one or more medical practitioners in one or more medical procedure rooms, the medical reference manual comprising a plurality of steps based on a plurality of operative reports associated with the medical procedure, and the system comprising:

one or more imaging devices, each imaging device configured to capture a plurality of video frames associated with an execution of the medical procedure;

a server communicatively coupled to the one or more imaging devices, and configured to receive the plurality of video frames from the one or more imaging devices, the server comprising:

a server processor configured to:

create one or more additional operative reports by processing the plurality of video frames, wherein the creating comprises:

identifying a medical item and the one or more medical practitioners in the plurality of video frames;

analyzing the plurality of video frames to determine one or more first parameters associated with the medical item and one or more second parameters associated with the one or more medical practitioners captured in the plurality of video frames;

associating the one or more first parameters of the medical item with the one or more second parameters of the one or more medical practitioners to identify one or more current steps being performed during the medical procedure; and creating the one or more additional operative reports for the medical procedure based on the one or more current steps being performed during the medical procedure; and continuously optimize, via a machine learning model implemented by the server processor, the plurality of steps in the medical reference manual for the medical procedure by:

analyzing the plurality of steps included in the medical reference manual and the one or more identified current steps included in the one or more additional operative reports to determine one or more optimal steps to be included in the medical reference manual, wherein determining the one or more optimal steps includes:

for each step in the medical reference manual:

obtain one or more outputs of one or more medical devices associated with the corresponding step in the medical reference manual;

determining an analogous step in the one or more additional operative reports;

obtaining one or more outputs of one or more medical devices associated with the analogous step in the one or more operative reports;

correlating, using the machine learning model, the one or more outputs of the one or more medical devices associated with the corresponding step in the medical reference manual and the one or more outputs of the one or more medical devices associated with the analogous step in the one or more additional medical procedures:

determining, using the machine learning model, the optimal step that results in desired one or more outputs of the one or more medical devices based on the correlation and data associated with the desired one or more outputs of the one or more medical devices;

modifying the medical reference manual based on the determination; and repeating the creating, the optimizing, and the modifying steps during the medical procedure to continuously optimize the medical reference manual.

2. The system of claim 1, wherein the server is configured to:

obtain subsequent operative reports associated with the combination of the medical procedure identifier, the medical practitioner identifier, and the medical procedure room identifier;

analyze, using the machine learning model, the optimal steps included in the medical reference manual and steps included in the subsequent operative reports to update the optimal steps; and modify the medical reference manual based on the updated optimal steps for the medical procedure.

3. The system of claim 1, wherein the one or more medical practitioners corresponds to a plurality of medical practitioners and the one or more medical procedure rooms corresponds to a plurality of medical procedure rooms, and wherein the one or more additional operative reports are associated with one or more of a plurality of medical practitioner identifiers identifying the plurality of medical practitioners performing the medical procedure and a plurality of medical procedure room identifiers identifying the plurality of medical procedure rooms for performing the medical procedure.

4. The system of claim 1, wherein the one or more first parameters include one or more of: a movement and time stamps associated with the movement of the medical item and a positioning and time stamps associated with the positioning of the medical item, and the one or more second parameters include one or more of: a movements and time stamps associated with the movement of the one or more medical practitioners and a positioning and time stamps associated with the positioning of the one or more medical practitioners.

5. The system of claim 1, wherein the server is configured to:

obtain the one or more outputs from the one or more medical devices associated with the medical procedure; and modify the one or more operative reports based on the one or more outputs.

6. The system of claim 1, wherein the server is further configured to:

update the optimal steps of the medical reference manual based on one or more user inputs.

7. The system of claim 1, wherein the server is further configured to:

update the operative report associated with the medical procedure based on one or more user inputs.

8. A method for continuously optimizing a medical reference manual for a medical procedure performed by one or more medical practitioners in one or more medical procedure rooms, the medical reference manual comprising a plurality of steps based on a plurality of operative reports associated with the medical procedure, and the method comprising:

capturing, by one or more imaging devices, a plurality of video frames associated with an execution of the medical procedure;

receiving, by a server, the plurality of captured video frames from the one or more imaging device;

creating, by the server, one or more additional operative reports by processing the plurality of video frames, wherein the creating comprises identifying a medical item and the one or more medical practitioners in the plurality of video frames;

analyzing, by the server, the plurality of video frames to determine one or more first parameters associated with the medical item and one or more second parameters associated with the one or more medical practitioners captured in the plurality of video frames;

associating, by the server, the one or more first parameters of the medical item with the one or more second parameters of the one or more medical practitioners to identify one or more current steps being performed during the medical procedure; and creating, by the server, the one or more additional operative reports for the medical procedure based on the one or more current steps being performed during the medical procedure;

continuously optimizing, by the server, the plurality of steps included in the medical reference manual for the medical procedure by:

analyzing, by the server, the plurality of steps included in the medical reference manual and the one or more identified current steps included in the one or more additional operative reports to determine one or more optimal steps to be included in the medical reference manual, wherein determining the one or more optimal steps includes:

for each step in the medical reference manual:

obtain one or more outputs of one or more medical devices associated with the corresponding step in the medical reference manual;

determining an analogous step in the one or more additional operative reports;

obtaining one or more outputs of one or more medical devices associated with the analogous step in the one or more operative reports;

correlating, using the machine learning model, the one or more outputs of the one or more medical devices associated with the corresponding step in the medical reference manual and the one or more outputs of the one or more medical devices associated with the analogous step in the one or more additional medical procedures:

determining, using the machine learning model, the optimal step that results in desired one or more outputs of the one or more medical devices based on the correlation and data associated with the desired one or more outputs of the one or more medical devices;

modifying, by the server, the medical reference manual based on the determination; and repeating, by the server, the creating, the optimizing, and the modifying steps during the medical procedure to continuously optimize the medical reference manual.

9. The method of claim 8, further including:

obtaining, by the server, subsequent operative reports associated with the combination of the medical procedure identifier, the medical practitioner identifier, and the medical procedure room identifier;

analyzing, by the server, the optimal steps included in the medical reference manual and steps included in the subsequent operative reports to update the optimal steps using the machine learning model; and modifying, by the server, the medical reference manual based on the updated optimal steps for the medical procedure.

10. The method of claim 8, wherein the one or more medical practitioners corresponds to a plurality of medical practitioners and the one or more medical procedure rooms corresponds to a plurality of medical procedure rooms, and wherein the one or more additional operative reports are associated with one or more of a plurality of medical practitioner identifiers identifying the plurality of medical practitioners performing the medical procedure and a plurality of medical procedure room identifiers identifying the plurality of medical procedure rooms for performing the medical procedure.

11. The method of claim 8, wherein the one or more first parameters include one or more of: a movement and time stamps associated with the movement of the medical item and a positioning and time stamps associated with the positioning of the medical item, and the one or more second parameters include one or more of: a movement and time stamps associated with the movement of the one or more medical practitioners and a positioning and time stamps associated with the positioning of the one or more medical practitioners.

12. The method of claim 8, further including:

obtaining, by the server, the one or more outputs from the one or more medical devices associated with the medical procedure; and modifying, by the server, the one or more operative reports based on the one or more outputs.

13. The method of claim 8, further including:

updating, by the server, the optimal steps of the medical reference manual based on one or more user inputs.

14. The method of claim 8, further including:

updating, by the server, the operative report associated with the medical procedure based on one or more user inputs.

* * * * *